(12) United States Patent
Stahl

(10) Patent No.: US 6,517,702 B2
(45) Date of Patent: *Feb. 11, 2003

(54) SENSOR FOR THE ANALYSIS OF EXHAUST GASES AND ANALYSIS METHOD

(75) Inventor: Roland Stahl, Freiberg (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/439,848

(22) Filed: Nov. 12, 1999

(65) Prior Publication Data

US 2002/0043461 A1 Apr. 18, 2002

(51) Int. Cl.$^7$ ............................................. G01N 27/407

(52) U.S. Cl. ..................... 205/784.5; 205/787; 204/424; 204/425; 204/426

(58) Field of Search ............................... 205/783.5, 784, 205/785, 787, 780.5; 204/424–429

(56) References Cited

U.S. PATENT DOCUMENTS

| | | | | |
|---|---|---|---|---|
| 4,226,692 A | * | 10/1980 | Isenberg | 204/424 |
| 4,985,126 A | * | 1/1991 | Haefele et al. | 204/787 |
| 5,993,641 A | * | 11/1999 | Okazaki et al. | 205/784.5 |
| 6,019,881 A | * | 2/2000 | Kurosawa et al. | 204/424 |
| 6,045,673 A | * | 4/2000 | Kato et al. | 204/425 |

FOREIGN PATENT DOCUMENTS

| | | | |
|---|---|---|---|
| EP | 0 731 351 A2 | * | 11/1996 |
| GB | 2288873 | * | 1/1995 |
| WO | 96-28722 | * | 9/1996 |

OTHER PUBLICATIONS

Logothetis et al. "High–Temperature Oxygen Sensors Based on Electrochemical Oxygen Pumping", pp. 136–154, ACS Symposium Series 309, 1986 (month unknown).*

Heslop et al., "Inorganic Chemistry", ISBN 0–444–41426–6, pp. 196–199, month unavail. 1976.*

Automotive Electronics Handbook. Section 6: "Exhaust Gas Sensors". McGraw Hill Inc. (1995)*. month unavail.

Serguei Somov et al., "Gas Analysis With Arrays Of Solid State Electrochemical Sensors: Implications to Minotor HCs and $NO_x$ In Exhausts," Sensors And Actuators B 35–36 (1996) 409–418.

S. I. Somov et al., "A Parallel Analysis Of Oxygen And Combustibles In Solid Electrolyte Amperometric Cells", Sensors and Actuators B 47 (1998), 131–138.

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

To determine the oxidizable portion of exhaust gases in the presence of the reducible portion with the legally required precision, a method and a sensor are disclosed for analyzing a flow of exhaust gas components. The sensor includes a limit current measurer, one limit current pump for reducible gases and, downstream from this pump in the direction of diffusion, another limit pump for oxidizable gases. The electrodes of the limit current pump for reducible gases are made of a material that does not catalyze the reaction between oxidizable and reducible gases.

25 Claims, 3 Drawing Sheets

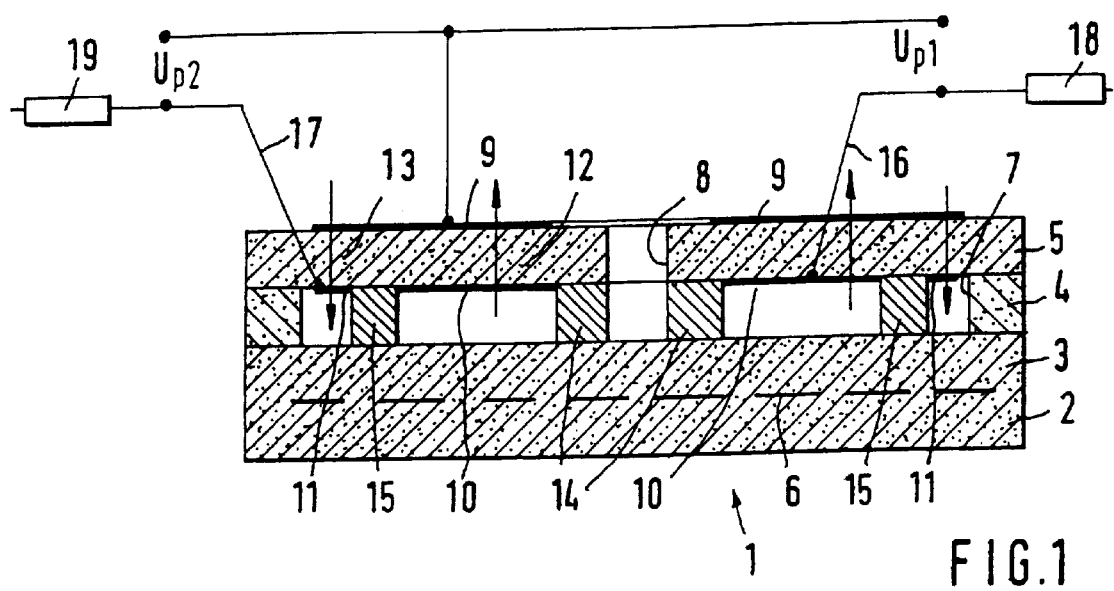
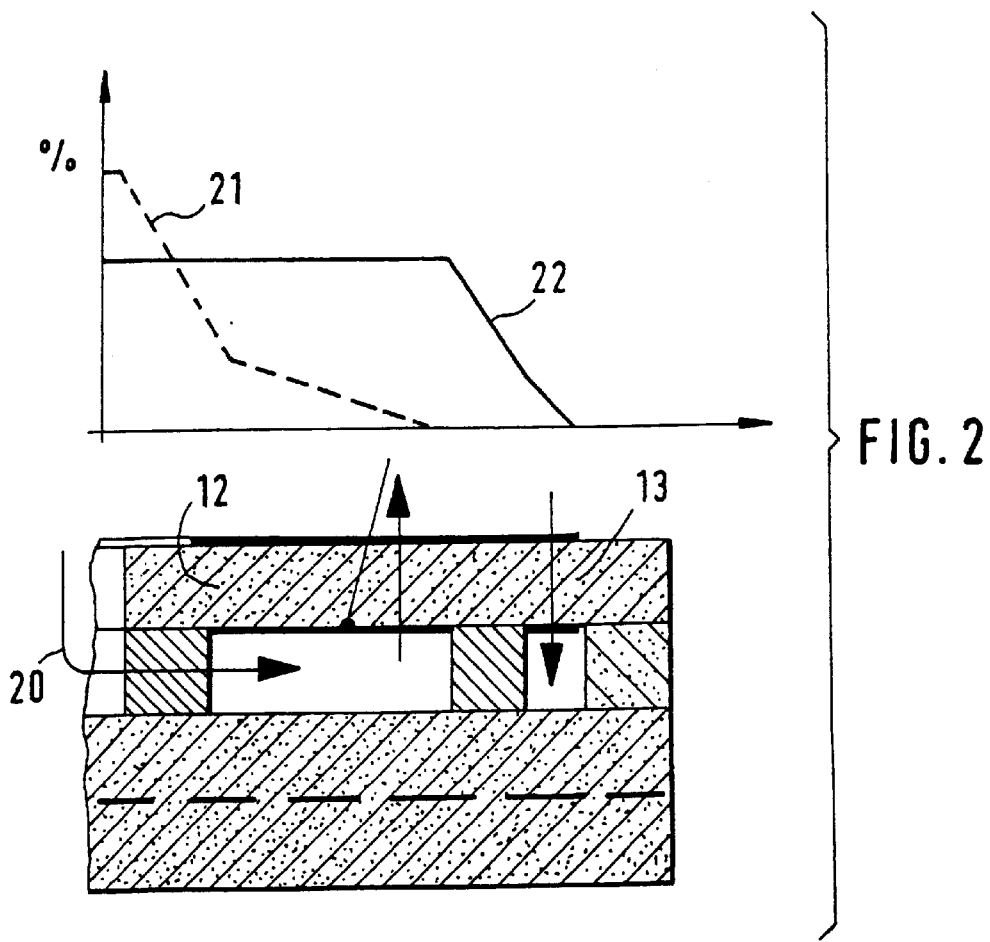

SENSOR FOR THE ANALYSIS OF EXHAUST GASES AND ANALYSIS METHOD

FIELD OF THE INVENTION

The present invention relates to a sensor for analyzing a stream of exhaust gas components, the sensor including a limit current measurer, and a method for determining exhaust gas components, in particular, by using the sensor.

BACKGROUND INFORMATION

A plurality of instruments for the analysis of exhaust gases of motor vehicles are described, for example, in the book "Automotive Electronics Handbook" (1995), McGraw Hill Inc., Section 6 "Exhaust Gas Sensors." Such instruments include, for example, the $\lambda=1$ probe, which is an equilibrium sensor that checks, by measuring the Nernst voltage, whether the air-fuel mixture injected into a gasoline engine has a $\lambda$ value of approximately one. The UEGO sensor (also known as the universal sensor) is also an equilibrium sensor, which is operated as a combination of a sensor based on the Nernst principle and a limit value probe, which are immersed in the exhaust gas of the internal combustion engine and whose measuring current, which depends on the $\lambda$ value, is used to regulate the $\lambda$ value. The operation of mixed-potential sensors, which are disequilibrium sensor type instruments, is based on the fact that reduced catalytic activity prevents a gas equilibrium from being established on the electrode of a $ZrO_2$ galvanic cell. As a result, no state of oxidation/reduction equilibrium can be established in oxygen and a mixed potential is formed, which is determined, among other things, by electrode activity, temperature, and gas composition. By "passively" measuring a signal dependent on the state of the electrode, mixed-potential sensors allow conclusions to be drawn concerning the gases in question. Their use in practice, however, is problematic, since they only operate properly in a very narrow temperature range, and their signal is often dependent on their history—their properties change as they age. A $NO_x$ pump sensor is also a disequilibrium sensor. It is used for determining $NO_x$ in the presence of oxygen. It operates as follows: oxygen is pumped out of a first cathodic limit current cell, the electrode being made of platinum-gold, which prevents $NO_x$ from also being pumped out. Therefore, a limit current, which is proportional to the $NO_x$ level in the exhaust gas, can be measured in a second cathodic limit current cell.

To date, there is no known field-usable method of determining the oxidizable components of exhaust gases in the presence of the reducible components with the accuracy required by law.

SUMMARY OF THE INVENTION

An object of the present invention is to provide such a method.

The sensor according to the present invention is a disequilibrium sensor having a simple design. Reducible and oxidizable gases can be analyzed by this single sensor, i.e., no separate sensors are needed for the two analyses. Analysis is performed using current limit probes. Current limit probes "actively" measure the diffusion characteristics. Their electrodes only have to pump and prevent catalysis or only allow anodic oxidation. Aging may necessitate a slight increase in the pump voltage to reach the limit current. The measured signal, however, is actually the diffusion resistance. The sensor according to the present invention contains no closed-circuit control, so no expensive electronic circuitry is needed. The sensor is well suited for measuring exhaust gases both in engines operated in the lean range, such as diesel engines, and in engines, such as gasoline engines, operated in the $\lambda=1$ range. The sensor according to the present invention can determine the sum of both reducible and oxidizable gases with considerable accuracy, so that it can often replace expensive, complex, and bulky analyzers. The sensor can also be used for on-board diagnostics (OBD). The operation of the sensor is based on the fact that, by suitably selecting the electrode material in the cathode cell, its catalytic activity is so low that, despite the very high temperatures, a reaction between reducible and oxidizable gases is almost impossible even if there is an excess of reducible exhaust gas components such as oxygen. The lowest possible catalytic activity of the electrode material can also be supported by appropriate material morphology, the most favorable morphology being determined by simple tests.

The electrode material of the cathode cell is advantageously made of platinum-gold.

The two limit current pumps can be advantageously mounted on a single substrate. This not only makes a very compact sensor arrangement possible, but also results in a sensor so similar to the UEGO sensor, that it can be manufactured on the UEGO sensor assembly line without considerable adjustments being required.

The limit current pump for oxidizable gases and the limit current pump for reducible gases can be advantageously operated at a constant pump voltage. The limit current pump for reducible gases can, however, also be operated at a pump voltage that is independent of the limit current to avoid decomposition of $H_2O$ and $CO_2$ in the exhaust gas.

In an advantageous embodiment of the sensor according to the present invention, at least two selective pump cells are provided for oxidizable gases, the electrode materials being selected so that in the cells upstream from the last cell in the direction of diffusion only the reaction of one oxidizable exhaust gas component is allowed. The materials are selected for their composition, with spinel advantageously added, for example, and for their morphology.

The oxidizable components of a lean exhaust gas and the reducible and oxidizable components of an exhaust gas with $\lambda=1$ can be advantageously determined using the method according to the present invention. This application is particularly advantageous, since it allows the efficiency of a three-way catalyst to be determined in the range from 0% to 100%. The A probes used so far only measure in the approximate range of 80% to 100%.

With the embodiment of the sensor according to the present invention having at least two pump cells for oxidizable gases, the carbon monoxide and ammonia or carbon monoxide and hydrocarbon levels can be advantageously determined side by side. Selectivity, for example, in the SCR method (see below), and detection of $NH_3$ in the presence of CO in the exhaust gas can be achieved by suitable actions on the system such as an upstream oxidation catalyst to oxidize CO prior to introducing $NH_3$ or its precursor.

BRIEF DESCRIPTION OF THE DRAWINGS

FIG. 1 schematically shows 1a cross section of an embodiment of a sensor according to the present invention.

FIG. 2 shows a detail of the embodiment illustrated in FIG. 1 and, in an associated diagram, the concentrations of the oxidizable exhaust gas components and the reducible exhaust gas components diffusing with the exhaust gas from the sensor inlet through the sensor plotted against the location coordinates.

DETAILED DESCRIPTION

Figure 3A:
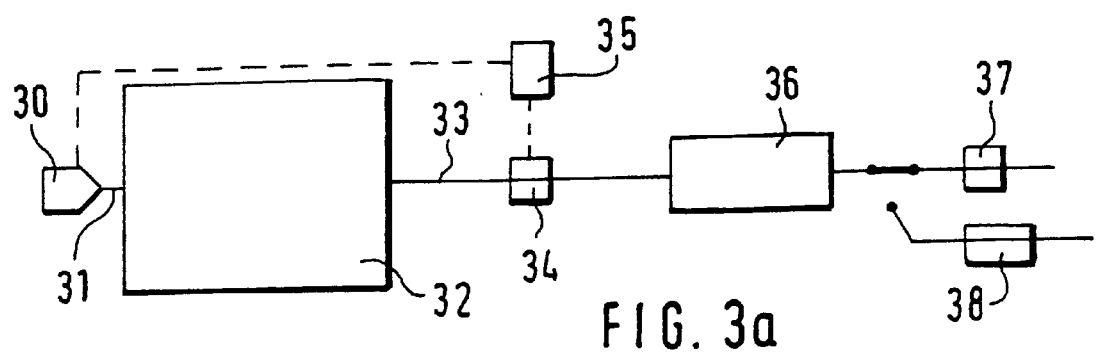
FIG. 3a schematically shows the path of a fuel mixture injected into a gasoline engine, through the engine, a first Nernst cell, the catalyst and then either through a second Nernst cell or through a sensor according to the present invention.

The embodiments of a sensor according to the present invention, described in the following, are particularly advantageous, but it should be pointed out that they are only named as examples, and a plurality of versions are possible within the framework of the present invention.

Sensor 1 illustrated in FIG. 1 has four consecutive ceramic layers 2, 3, 4, and 5. An electric heater 6 is arranged at the boundary between layers 2 and 3. Layer 4 has a preferably circular through orifice 7, and layer 5 has a relatively small through orifice 8, which is concentric to orifice 7. An annular electrode 9, whose outer diameter is approximately equal to the diameter of orifice 7 and whose inner diameter is somewhat greater than the diameter of opening 8, is mounted on the outside of layer 5. Two annular electrodes 10 and 11, which do not touch, are mounted on the inside of layer 5 concentrically to one another and to electrode 9, the outer diameter of electrode 11 being approximately equal to the outer diameter of opening 7 and the inner diameter of electrode 10 being approximately equal to the inner diameter of electrode 9. Electrodes 9, 10, and 9, 11 each form a limit current cell 12, 13. Diffusion resistors 14 and 15, forming annular barriers in orifice 7, are preferably mounted between orifice 8 and electrode 10 and between electrodes 10 and 11. Pump voltages $U_{p1}$ and $U_{p2}$ are applied between electrodes 9, 10 and 9, 11, both of which voltages are constant. As an alternative, $U_{p1}$ is dependent on limit current $I_{gr1}$ generated ($U_{p1}=a+b \cdot I_{gr1}$) The dependence is achieved using a conventional electronic circuit. Electrodes 10 and 11 are contacted by conductors 16 and 17, which conduct away limit currents $I_{gr1}$ and $I_{gr2}$, whose intensities are measured by measuring resistors 18 and 19, respectively. The arrows perpendicular to the electrodes indicate the directions of the $O^{--}$ ion flows in the limit current cells.

Electrode 10 is made of a material that virtually does not catalyze the oxidation of oxidizable exhaust gas components in the presence of oxidizing agents. The catalytic action, or rather non-action, of the electrode material can also be influenced by its morphology. Such a material is platinum-gold, for example. An advantageous material for electrode 11 is platinum-rhodium.

Initially we shall elucidate the use of sensor 1 for the detection of oxidizable gases in lean exhaust gases.

As FIG. 2 shows, exhaust gas 20 to be analyzed enters sensor 1 through orifice 8 and diffuses past electrodes 10 and 11. All reducible gases of the exhaust gas are removed by suction in limit current probe 12 by a cathodic limit current. This is illustrated by curve 21 in the diagram of FIG. 2, where concentration is plotted against the path traveled by the gas in the sensor. The reducible gases (in particular, oxygen) and oxidizable gases should not react with one another. To prevent hydrocarbons (HC), for example, from reacting with oxygen, high temperatures and catalytic reactions must be avoided. On the other hand, limit current cells require certain minimum temperatures, which are the higher the higher the limit current. A compromise must therefore be found. When lean mixtures are analyzed, the sensor will operate between approximately 700° and approximately 800° C. The temperature effect is partially eliminated by the very high spatial velocity of the exhaust gas in orifice 7, which prevents the establishment of thermodynamic equilibrium. In particular, however, a reaction is avoided when electrode 10 (cathode) is made of a material that has little or no catalytic action. Such a material is platinum-gold, for example. A catalytic effect can also be reduced by suitably configuring the diffusion path (gas phase diffusion, Knudsen diffusion).

The cathodic limit current can be measured in measuring resistor 18. Its value, however, is of little importance if the exhaust gas is lean, since the reducible gas is made up mainly of oxygen. Pump cell 12 can be operated at a constant pump voltage. If $H_2O$ and/or $CO_2$ are reduced, then it causes no problem if the $H_2$ or CO obtained immediately react with $O_2$. With very inactive electrodes 10, it may be advantageous, however, to work with a current-dependent pump voltage ($U_p=a+bI_{gr}$) (see above) to avoid the reduction of $H_2O$ and $CO_2$.

HC, carbon monoxide (CO) and ammonia ($NH_3$) are particularly important as oxidizable gases. $NH_3$ gets into the exhaust gas in the selective catalytic reduction (SCR) process, if more $NH_3$ is added to decompose $NO_x$, for example, in the form of a precursor such as urea, than is needed for reacting the $NO_x$ present. As curve 22 in FIG. 2 shows, the oxidizable gases are anodically oxidized in limit current cell 13. The sum of concentrations of oxidizable gases is determined from the intensity of the anodic limit current. Since the concentrations of the oxidizable gases are low and the anodic limit current is also low, heater interference may occur. However, since it also occurs in the cathodic limit current, current peaks that occur simultaneously in both limit currents can be filtered out.

Engines that run in the lean range are diesel engines and, occasionally, BDE engines.

Sensor 1 can be used at temperatures between approximately 600° and approximately 700° C., preferably also to detect reducible and oxidizable gases in mixtures in the λ=1 range, in particular, for catalyst monitoring. In this area also the concentration of reducible gases are relevant; therefore, the anodic and cathodic limit currents are measured and used for determining concentration.

Figure 3B:
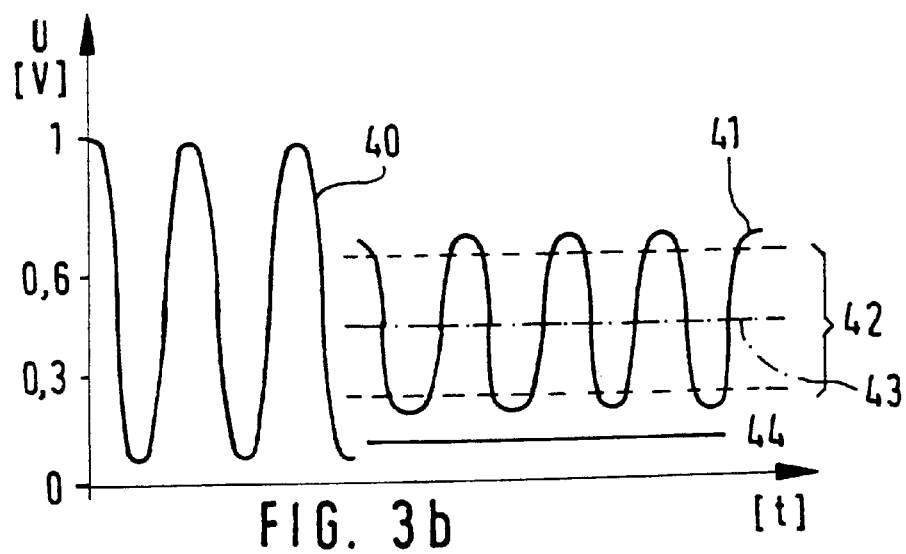
FIG. 3b shows, in a diagram, the Nernst voltage measured at the first Nernst cell of FIG. 3a and the Nernst voltage, measured at the second Nernst cell in different operating states, plotted against time.

Exhaust gases of engines operating near $\lambda=1$ only contain a small amount of oxygen. Reducible components such as $NO_x$ and oxidizable components such as $CO$, $H_2$, and HC may occur in the exhaust as harmful gases and are brought to very low values by catalysts. Today's technology makes it possible to control engines very accurately. However, engines operated with a three-way catalyst should not be regulated at $\lambda=1$. They should rather be operated on either side of $\lambda=1$ (for example, $\lambda=0.975$ to 1.025) using a precisely balanced "pendulum mode" to allow the harmful gases to be eliminated in the exhaust gas. FIG. 3a, schematically shows an arrangement composed of a gasoline engine and a catalyst, including an injection pump, various sensors, and a controller. The fuel mixture having the predefined composition is injected from injection pump 30 via line 31 into engine 32, where it undergoes combustion. The exhaust gas is removed from the engine through line 33 and passed through a Nernst probe 34. Due to the "pendulum mode," signal 40 of Nernst probe 34, a $\lambda=1$ probe, has the shape shown in FIG. 3b, which is symmetric to the voltage corresponding to $\lambda=1$ (450 mV). If the signal deviates from that shape, the composition of the fuel-air mixture is modified using controller 35 as a function of signal 40. After having passed through Nernst probe 34, the exhaust gas passes through 3-way catalyst 36 and may pass through an on-board diagnosis I (OBD I) probe 37, which is another $\lambda=1$ probe. Depending on the operating state, Nernst probe 37 returns signals 41, 43, and 44 shown in the diagram of FIG. 3b. Signal 41, which emulates the pendulum waves, shows that the catalyst is not working in an optimum manner. Curve 41, however, only shows that the efficiency of the catalyst is about 80% or less. This conclusion is imprecise, since a catalyst is still usable even with an efficiency of 50%. Signals 43 and 44 form straight lines, which means that the catalyst is working (efficiency>80%), i.e., it succeeded in equalizing the pendulum movements. Signal 43 is situated within the range between approximately 300 and approximately 600 mV, delimited by straight lines 42. This leads to the conclusion that the engine is controlled by the means to work at $\lambda=1$. Signal 44 is less than 300 mV. This leads to the conclusion that the fuel-air mixture is too lean, and the engine control is not working in an optimum manner.

Figure 3C:
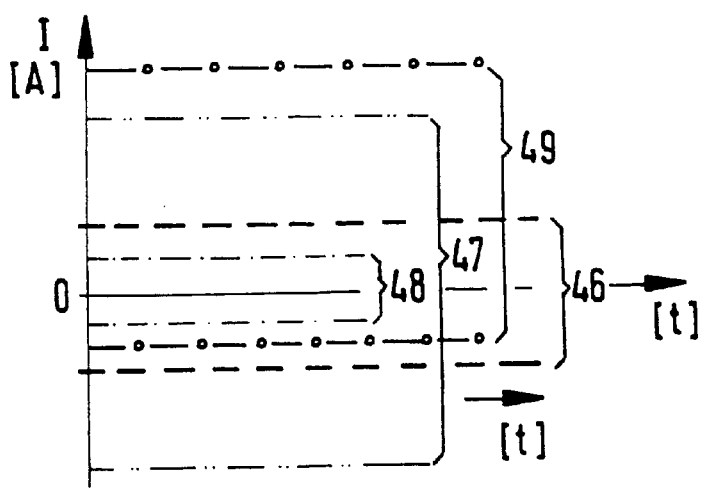
FIG. 3c shows, in a diagram, the limit currents of reducible and oxidizable exhaust components measured in three different operating states in the sensor of FIG. 3a, plotted against time.

If Nernst probe 37 is replaced with sensor 1 (reference No. 38), two signals 47, 48, 49 are obtained in each of the three different operating states, as shown in the diagram of FIG. 3c. Signals 47 are approximately symmetrical to the zero line. This means that the engine control operates properly. However, signals 47 are too far apart, which means that the exhaust gas still contains considerable amounts of reducible and oxidizable components, which indicates that the catalyst has a limited efficiency. Signal 47 not only allows one to draw a quantitative conclusion on the proportion of reducible and oxidizable exhaust gas components, but also on the degree of remaining catalyst efficiency, not only in the range between 80% and 100%, but also between 0% and 100%. This is very important in practice, since it allows catalysts to be used for a considerably longer time than is possible today. Signals 48 are symmetric to the zero line, which again shows proper engine control, but they are so close to the zero line that they are within the area delimited by lines 46, which define the upper limits of the legally allowed level of reducible and oxidizable contaminants. Proximity to the zero line proves that the catalyst is working in an optimum manner. Signals 49 are obtained when the exhaust gas composition is too close to the lean range, which means that the engine control is not working properly. The signals allow conclusions to be drawn on the catalyst quality and the proportion of reducible and oxidizable exhaust gas components as in the cases characterized by signals 47 and 48. To draw a quantitative conclusion on pollutants in the exhaust gas, the related art would have required analysis using expensive and bulky instruments such as an IR spectrometer. Sensor 1 meets the basic requirements for use in OBD II.

Figure 4:
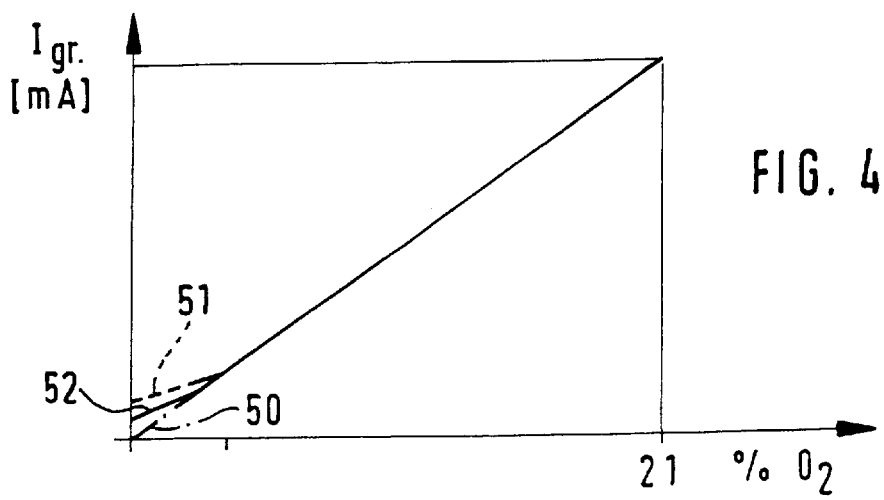
FIG. 4 shows, in a diagram, the measured limit current of an $O_2$-containing gas plotted against $O_2$ concentration, taking into consideration both when the gas contains no $H_2O$ or $CO_2$ and when the gas contains $H_2O$ and $CO_2$, the limit current being given for two pump voltages in the latter case.
Figure 5:
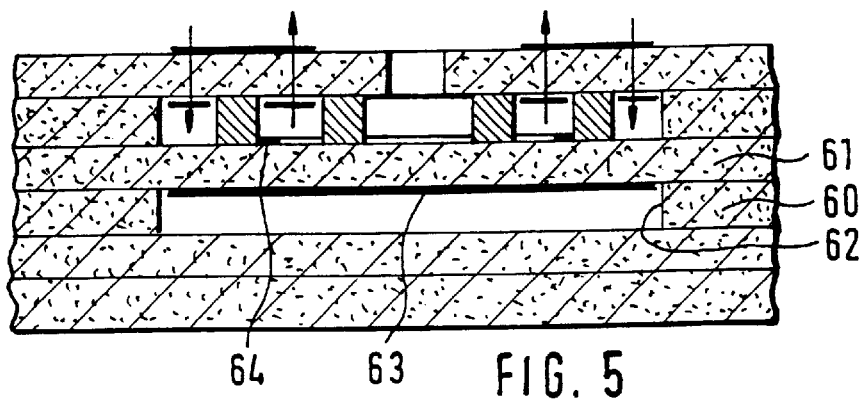
FIG. 5 schematically shows another embodiment of the sensor according to the present invention.

The proportions of reducible and oxidizable gases measured using sensor 1 are proportional to the measured limit currents $I_{gr}$. The reducible gas present in the greatest proportion is oxygen. If a pump voltage of about 800 mV is used, the proportionality between limit current and $O_2$ level is linear for higher $O_2$ levels. For $O_2$ levels<2%, which is particularly interesting for the $\lambda=1$ range, if the exhaust gas contains $H_2O$ and $CO_2$, there is deviation from linearity, caused by the reduction of $CO_2$ and $H_2O$ with liberation of $O_2$. The diagram of FIG. 4, where the limit current is plotted against the $O_2$ level in air (21% oxygen) (curve 50) and against a gas mixture, which contains $CO_2$ and $H_2O$ in addition to oxygen, shows this relationship with curves 51 and 52. Curves 51 and 52 differ in that the underlying pump voltage is 800 mV for curve 51 and 600 mV for curve 52. It can be seen that for the lower voltage, there is less deviation from linearity. From at least this fact the inventor derived the idea to make pump voltage dependent on the limit current according to the equation $U_p=a+b\cdot I_{gr}$ (see above). As an alternative, he integrated a Nernst cell into sensor 1. The sensor thus modified is illustrated in FIG. 5, where a ceramic plate 60 next to plate 3 and a ceramic plate 61 next to ceramic plate 60 are inserted between ceramic plates 3 and 4. Plate 61 has a through orifice 62, which can have the same bottom face as, and can be arranged concentrically to, orifice 7. Orifice 62 is connected to outside air and is used as air reference. The surface of plate 4 adjacent to orifice 62 is covered with a metal electrode 63, and in the cathode chamber of orifice 7, an annular electrode 64, which is concentric with orifice 7, is mounted on the surface of the plate adjacent to orifice 62. The Nernst cell is controlled in the traditional manner. The cathodic current is controlled so that the voltage of the Nernst cell is 450 mV, for example. This results in that only the amount of gas required for keeping the anodic part in the $\lambda$ range is removed by suction in the cathode part, thus guaranteeing that $H_2O$ and $CO_2$ are not decomposed.

Figure 6:
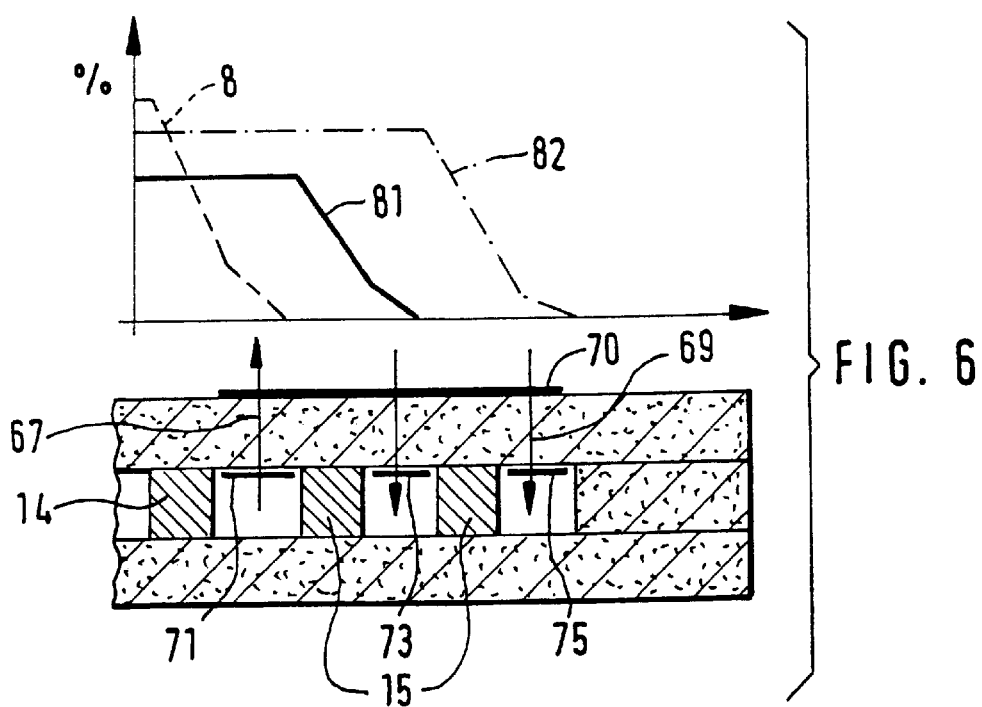
FIG. 6 schematically shows a cross section through a detail of another embodiment, suitable for selective determination of two oxidizable exhaust gas components, of the sensor according to the present invention and, in an associated diagram, the concentrations measured using an exhaust gas probe, of the two oxidizable exhaust gas components and the reducible exhaust gas components diffusing from the sensor inlet through the sensor plotted against the location coordinates.

FIG. 6 shows a cross sectional detail of a sensor, which has a cathode cell 67 with electrodes 70 and 71 and two anode cells 68 and 69 with electrodes 70, 73 and 70, 75 in opening 7. The sensor of FIG. 6 differs from those shown in FIGS. 1 through 3 by the additional anode cell 68. It is used to selectively and separately determine two oxidizable gases in the exhaust gas. To achieve such selectivity, electrode 73 must be made of a material that only catalyzes the oxidation of one of the oxidizable gases. Such materials have been found during the development of mixed-potential sensors. It is spinel containing cobalt and chromium. The composition that is suitable for the special case and the suitable morphology of the electrode to selectively oxidize a gas can be determined by simple tests. For example, to determine CO and HC or CO and $NH_3$ separately in an exhaust gas in the $\lambda=1$ range, CO is oxidized in the first anodic cell 68 after the reducible gases have been removed in the cathodic cell (electrodes 70 and 71), and HC and $NH_3$ are oxidized in the second anodic cell 69. The procedures are illustrated in the diagrams of FIG. 6, where the gas concentrations are plotted against the distance traveled by gas diffusion, curve 80 being that of the reducible gases, curve 81 of CO, and curve 82 of HC and NH$_3$. Electrode 71 is made of Pt—Au; electrode 73 contains CoCrMnO$_4$, and electrode 75 is made of Pt—Rh.

The sensor detail shown in FIG. 6 can belong to a sensor in which the cathode cell is operated at a constant voltage (according to the equation U$_p$=a+b·I$_{gr}$) as in the case of sensor 1 (FIG. 1), or is similar to the sensor of FIG. 5.

What is claimed is:

1. A sensor for analyzing a stream of components in an exhaust gas, comprising:
    a first limit current pump having a first limit current, the first limit current pump reducing reducible gases;
    a first diffusion resistor positioned within an orifice which permits the stream of exhaust gas to enter the first limit current pump;
    a second limit current pump having a second limit current, the second limit current pump oxidizing oxidizable gases, wherein a second diffusion resistor is positioned in an orifice which permits the stream of exhaust gas to enter the second limit current pump;
    a first electrode associated with the first limit current pump, wherein the first electrode includes an electrode material that does not catalyze a reaction between the oxidizable gases and the reducible gases;
    a second electrode associated with the second limit current pump;
    a substrate on which are mounted the first limit current pump and the second limit current pump, wherein the first limit current pump and the second limit current pump share a common electrode that is exposed to the exhaust gas; and
    a circuit arrangement coupled to the first limit current pump through a first conductor path to the first electrode and to the second limit current pump through a second conduction path to the second electrode, wherein the circuit arrangement applies a first voltage across the first limit current pump via the first conduction path and applies a second voltage across the second limit current pump via the second conduction path, and farther wherein the circuit arrangement measures the first limit current passing across the common electrode and through the first conduction path and measures the second limit current passing across the common electrode and through the second conduction path.

2. The sensor according to claim 1, wherein the electrode material associated with the first electrode includes a platinum-gold material.

3. The sensor according to claim 1, further comprising:
    a substrate on which are mounted the first limit current pump and the second current limit pump.

4. The sensor according to claim 1, wherein the second limit current pump is operated at a constant pump voltage.

5. The sensor according to claim 1, wherein the first limit current pump is operated at one of a constant pump voltage and a pump voltage that correlates with the first limit current.

6. The sensor according to claim 5, wherein the pump voltage that is dependent on the limit current is electronically controlled according to a relation:

$$U_p = a + b \cdot I_{gr}$$

where U$_p$ is the pump voltage,
I$_{gr}$ is the limit current, and
a, b are constants of the relation.

7. The sensor according to claim 5, wherein the Nernst cell is arranged in a cathode chamber, where the cathode chamber lies between the first diffusion resistor and the second diffusion resistor.

8. The sensor according to claim 1, wherein the second limit current pump includes a first pump cell and a second pump cell, the first pump cell and the second pump cell oxidizing the oxidizable gases, the second pump cell being disposed downstream in the direction of diffusion with respect to the first pump cell, the first pump cell selectively oxidizing only one of the oxidizable gases, electrode materials of the first pump cell and the second pump cell being selected with respect to at least one of composition and morphology.

9. The sensor according to claim 8, wherein the first pump cell and the second pump cell are provided for an anode chamber lies between the first diffusion resistor and the second diffusion resistor.

10. The sensor according to claim 9, wherein the electrode material of the first pump cell includes a cobalt-chromium spinel.

11. The sensor according to claim 9, wherein the electrode material of the first pump cell includes a cobalt-chromium-manganese spinel.

12. A method for determining levels of reducible components and oxidizable components in an exhaust gas, comprising the steps of:
    diffusing the exhaust gas through a first limit current pump which includes a first limit current and a first electrode, where the first limit current pump reduces reducible gases, wherein the first electrode includes an electrode material that does not catalyze a reaction between the oxidizable gases and the reducible gases;
    diffusing the exhaust gas through a second limit current pump which includes a second limit current and a second electrode, wherein the second limit current pump oxidizes oxidizable gases, wherein the first limit current pump and the second limit current pump share a common electrode that is exposed to the exhaust gas, and are mounted on a substrate; and
    measuring the first limit current and the second limit current passing across the common electrode via a circuit arrangement, the circuit arrangement being coupled to the first limit current pump through a first conduction path and to the second limit current pump through a second conduction path, wherein a first voltage to operate the first current limit pump is applied through the first conduction path and a second voltage to operate the second current limit pump is applied through the second conduction path, and further wherein the levels of reducible components and oxidizable components correlate with the measured values of the first limit current and the second limit current.

13. The method according to claim 12, further comprising the step of:
    determining the levels of the oxidizable components of a lean exhaust gas.

14. The method according to claim 13, further comprising the step of:
    determining the levels of the reducible components of the lean exhaust gas.

15. The method according to claim 14, wherein the step of determining is performed at temperatures between approximately 700° and approximately 800° C.

16. The method according to claim 13, wherein the step of determining is performed at temperatures between approximately 700° and approximately 800° C.

17. The method according to claim 12, further comprising the step of:

determining the levels of the reducible components and the oxidizable components of the exhaust gas having $\lambda \approx 1$.

18. The method according to claim 17, wherein the step of determining is performed at temperatures between approximately 600° and approximately 700° C.

19. The method according to claim 12, further comprising the step of:
determining a sum of proportions of the oxidizable components.

20. The method according to claim 12, further comprising the step of:
determining proportions of individual oxidizable components.

21. The method according to claim 20, wherein the step of determining the proportions of the individual oxidizable components includes the step of determining a proportion of ammonia.

22. The method according to claim 20, wherein the step of determining proportions of the individual oxidizable components includes the step of selectively determining levels of two oxidizable components.

23. The method according to claim 22, wherein the two oxidizable components are one of (A) carbon monoxide and ammonia and (B) carbon monoxide and hydrocarbons.

24. The method according to claim 22, further comprising the step of:
determining proportions of the reducible components.

25. The method according to claim 24, further comprising the step of:
avoiding decomposition of $CO_2$ and $H_2O$.

* * * * *

UNITED STATES PATENT AND TRADEMARK OFFICE
CERTIFICATE OF CORRECTION

PATENT NO.    : 6,517,702 B2
DATED         : February 11, 2003
INVENTOR(S)   : Roland Stahl It is certified that error appears in the above-identified patent and that said Letters Patent is hereby corrected as shown below:

Column 2,
Line 50, change "A" to -- $\lambda$ --.
Line 63, change "1a" to -- a --.

Column 7,
Line 66, change "wherein the Nernst" to -- wherein a Nernst --.

Column 8,
Line 15, delete "chamber lies between the first diffusion resistor and" and insert -- chamber of the sensor where the anode chamber lies beyond --.

Signed and Sealed this

First Day of June, 2004

JON W. DUDAS
*Acting Director of the United States Patent and Trademark Office*